(12) United States Patent
Ravetch et al.

(10) Patent No.: US 9,481,724 B2
(45) Date of Patent: Nov. 1, 2016

(54) HDC-SIGN BINDING PEPTIDES

(71) Applicants: The Rockefeller University, New York, NY (US); Sloan-Kettering Institute for Cancer Research, New York, NY (US)

(72) Inventors: Jeffrey Ravetch, New York, NY (US); Andrew Pincetic, New York, NY (US); Ping Wang, New York, NY (US); Sam Danishefsky, Englewood, NJ (US)

(73) Assignees: The Rockefeller University, New York, NY (US); Sloan-Kettering Institute for Cancer Research, New York, NY (US)

( * ) Notice: Subject to any disclaimer, the term of this patent is extended or adjusted under 35 U.S.C. 154(b) by 217 days.

(21) Appl. No.: 14/366,528

(22) PCT Filed: Dec. 10, 2012

(86) PCT No.: PCT/US2012/068782
§ 371 (c)(1),
(2) Date: Jun. 18, 2014

(87) PCT Pub. No.: WO2013/095973
PCT Pub. Date: Jun. 27, 2013

(65) Prior Publication Data
US 2015/0110807 A1    Apr. 23, 2015

Related U.S. Application Data

(60) Provisional application No. 61/577,495, filed on Dec. 19, 2011.

(51) Int. Cl.
| | |
|---|---|
| *A61K 38/16* | (2006.01) |
| *C07K 16/18* | (2006.01) |
| *A61K 31/7028* | (2006.01) |
| *A61K 38/17* | (2006.01) |
| *C07K 14/47* | (2006.01) |
| *C07H 7/02* | (2006.01) |
| *C07K 14/705* | (2006.01) |
| *A61K 38/00* | (2006.01) |
| *A61K 39/00* | (2006.01) |

(52) U.S. Cl.
CPC ........... *C07K 16/18* (2013.01); *A61K 31/7028* (2013.01); *A61K 38/16* (2013.01); *A61K 38/1709* (2013.01); *C07H 7/02* (2013.01); *C07K 14/47* (2013.01); *C07K 14/705* (2013.01); *A61K 38/00* (2013.01); *A61K 2039/505* (2013.01); *C07K 2316/95* (2013.01)

(58) Field of Classification Search
None
See application file for complete search history.

(56) References Cited

U.S. PATENT DOCUMENTS

2009/0041770 A1*  2/2009  Chamberlain ....... C07K 16/082
424/134.1

FOREIGN PATENT DOCUMENTS

| EP | 2233502 | 9/2010 |
|---|---|---|
| WO | WO2008/109757 | 9/2008 |
| WO | WO2013/095973 | 6/2013 |

OTHER PUBLICATIONS

"Human IgG1 heavy chain, HCH2 region (residues 216-340), SEQ ID: 10.," Database Geneseq, XP002745196, Nov. 27, 2008.
Extended European Search Report in corresponding EP Application No. 12859843.0, dated Oct. 20, 2015, pp. 1-9.

* cited by examiner

*Primary Examiner* — Maury Audet
*Assistant Examiner* — Fred Reynolds
(74) *Attorney, Agent, or Firm* — Fish & Richardson P.C.

(57) ABSTRACT

Polypeptides that bind to DC-SIGN and/or its homologues and methods for using such peptides for the treatment of various disorders are described. DC-SIGN and its homologues are receptors that bind IgG antibodies or Fc fragments and mediate intravenous immunoglobulin (IVIG)-related reversal of inflammation associated with various immune disorders.

21 Claims, 8 Drawing Sheets

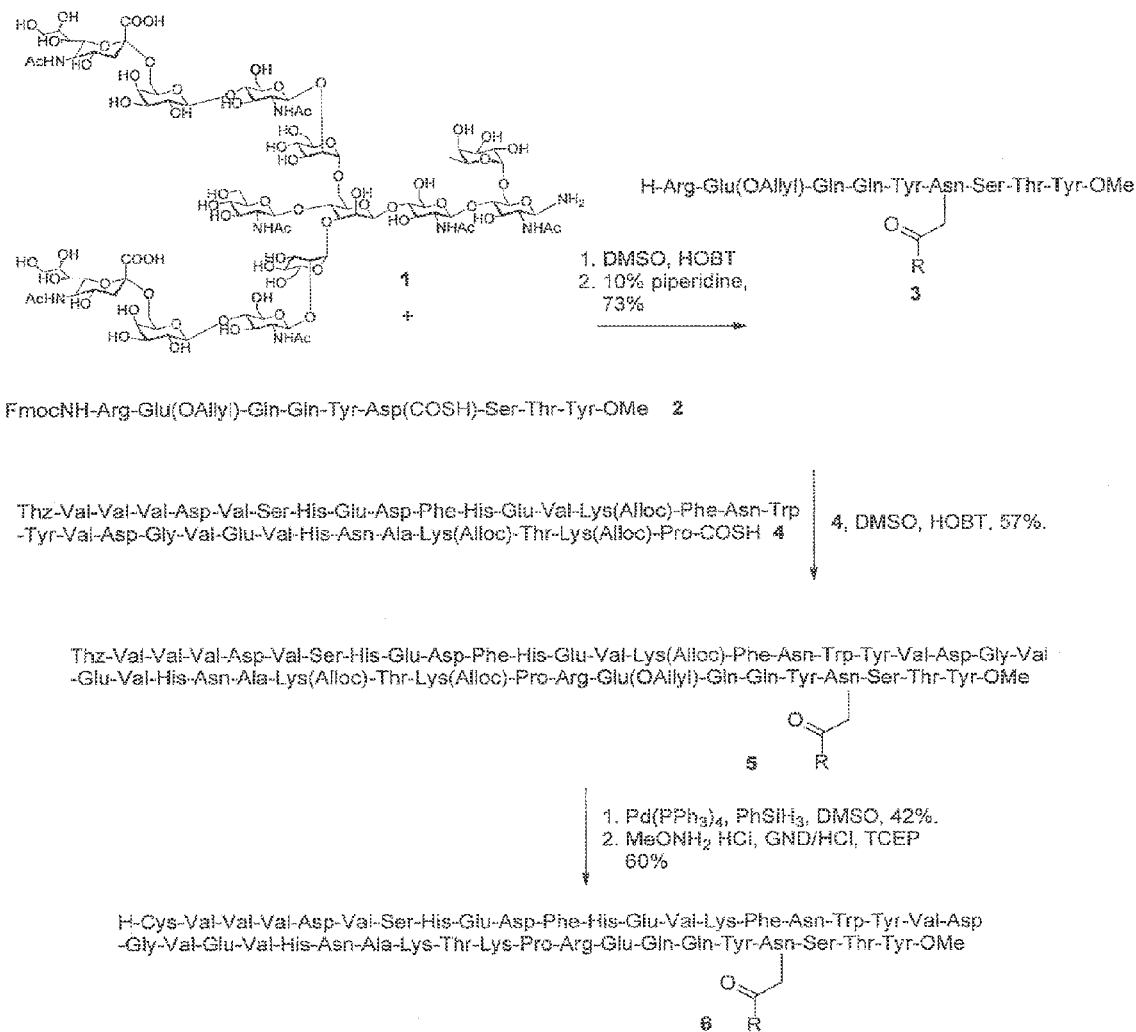

monoer peptide sequence
three letter aminoacid

H-Cys-Val-Val-Val-Asp-Val-Ser-His-Glu-Asp-Phe-His-Glu-Val-Lys-Phe-Asn-Trp-Tyr-Val-Asp
-Gly-Val-Glu-Val-His-Asn-Ala-Lys-Thr-Lys-Pro-Arg-Glu-Gln-Gln-Tyr-Asn-Ser-Thr-Tyr-OMe one letter aminoacid H-CVVVDVSHEDPHEVKFNWYVDGVEVHNAKTKPREQQYNSTY-OMe

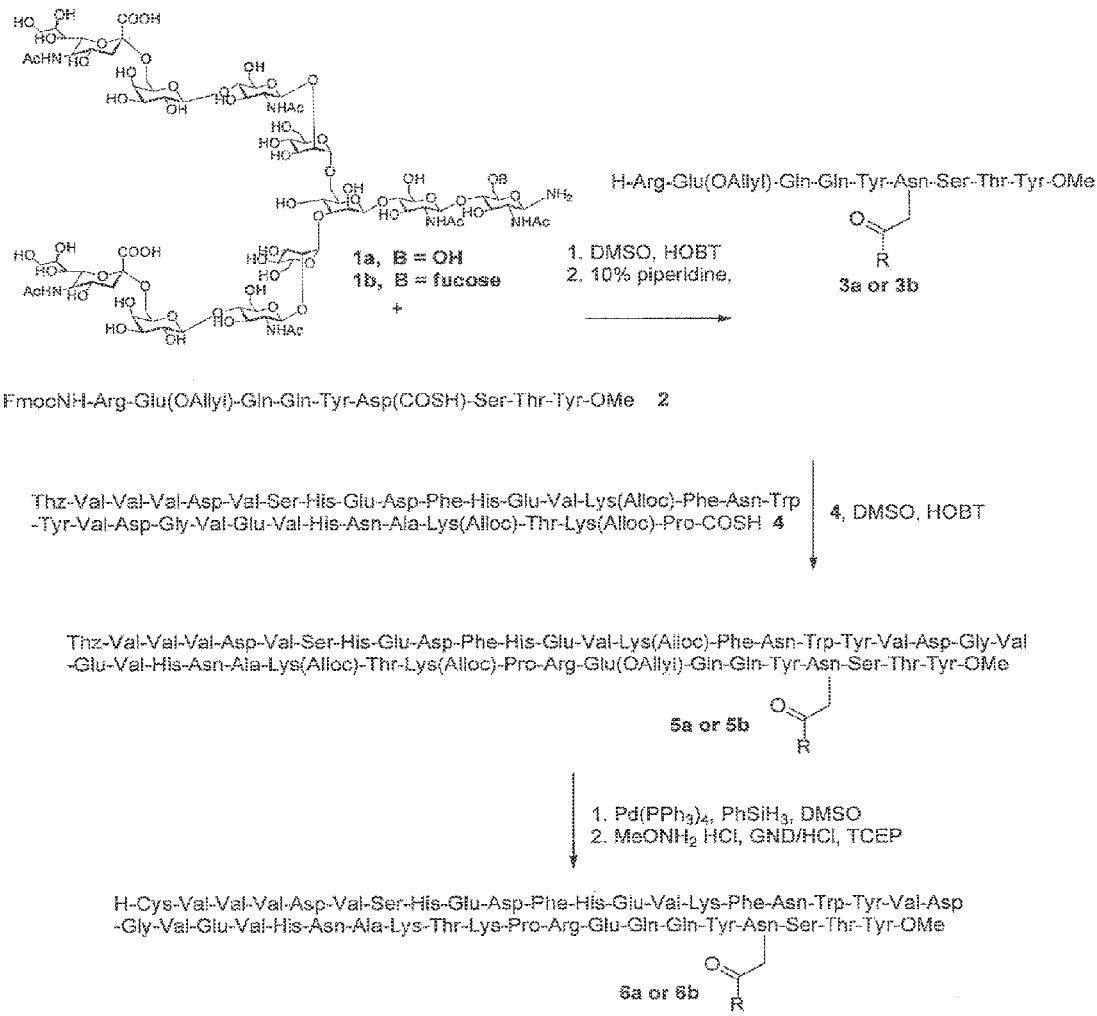

Synthetic a2,6sial IgG fragment appears to bind DC-SIGN with reduced affinity $K_{D1} = 1.33\ \mu M$ $K_{D2} = 14.3\ \mu M$

Fig. 3D

SEQUENCE LISTING

```
<160> NUMBER OF SEQ ID NOS: 9

<210> SEQ ID NO 1
<211> LENGTH: 40
<212> TYPE: PRT
<213> ORGANISM: Homo sapiens

<400> SEQUENCE: 1

Val Val Val Asp Val Ser His Glu Asp Pro His Glu Val Lys Phe Asn
1               5                   10                  15
```

Trp Tyr Val Asp Gly Val Glu Val His Asn Ala Lys Thr Lys Pro Arg
            20                  25                  30

Glu Gln Gln Tyr Asn Ser Thr Tyr
            35                  40

<210> SEQ ID NO 2
<211> LENGTH: 41
<212> TYPE: PRT
<213> ORGANISM: Artificial Sequence
<220> FEATURE:
<223> OTHER INFORMATION: Has a C in the N terminus

<400> SEQUENCE: 2

Cys Val Val Asp Val Ser His Glu Asp Pro His Glu Val Lys Phe
1               5                   10                  15

Asn Trp Tyr Val Asp Gly Val Glu Val His Asn Ala Lys Thr Lys Pro
            20                  25                  30

Arg Glu Gln Gln Tyr Asn Ser Thr Tyr
            35                  40

<210> SEQ ID NO 3
<211> LENGTH: 41
<212> TYPE: PRT
<213> ORGANISM: Artificial Sequence
<220> FEATURE:
<223> OTHER INFORMATION: glycosylated Asn at position 38

<400> SEQUENCE: 3

Cys Val Val Asp Val Ser His Glu Asp Pro His Glu Val Lys Phe
1               5                   10                  15

Asn Trp Tyr Val Asp Gly Val Glu Val His Asn Ala Lys Thr Lys Pro
            20                  25                  30

Arg Glu Gln Gln Tyr Asn Ser Thr Tyr
            35                  40

<210> SEQ ID NO 4
<211> LENGTH: 447
<212> TYPE: PRT
<213> ORGANISM: Homo sapiens

<400> SEQUENCE: 4

Glu Val Gln Leu Val Glu Ser Asp Gly Gly Leu Val Gln Pro Gly Arg
1               5                   10                  15

Ser Leu Lys Leu Pro Cys Ala Ala Ser Gly Phe Thr Phe Ser Asp Tyr
            20                  25                  30

Tyr Met Ala Trp Val Arg Gln Ala Pro Thr Lys Gly Leu Glu Trp Val
            35                  40                  45

Ala Ser Ile Ser Tyr Asp Gly Ser Thr Tyr Tyr Arg Asp Ser Val
        50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Gly Arg His Ser Ser Tyr Phe Asp Tyr Trp Gly Gln Gly Val Met Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro His Glu
            260                 265                 270

Val Lys Phe Asn Trp Tyr Val Asp Gly Val Glu Val His Asn Ala Lys
        275                 280                 285

Thr Lys Pro Arg Glu Gln Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 5
<211> LENGTH: 238
<212> TYPE: PRT
<213> ORGANISM: Homo sapiens

<400> SEQUENCE: 5

Lys Val Asp Lys Arg Val Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
```

```
              65                  70                  75                  80
Lys Pro Arg Glu Glu Gln Tyr Asn Ser Thr Tyr Arg Val Val Ser Val
                      85                  90                  95

Leu Thr Val Leu His Gln Asp Trp Leu Asn Gly Lys Glu Tyr Lys Cys
                100                 105                 110

Lys Val Ser Asn Lys Ala Leu Pro Ala Pro Ile Glu Lys Thr Ile Ser
                115                 120                 125

Lys Ala Lys Gly Gln Pro Arg Glu Pro Gln Val Tyr Thr Leu Pro Pro
130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
                180                 185                 190

Gly Ser Phe Phe Leu Tyr Ser Lys Leu Thr Val Asp Lys Ser Arg Trp
                195                 200                 205

Gln Gln Gly Asn Val Phe Ser Cys Ser Val Met His Glu Ala Leu His
                210                 215                 220

Asn His Tyr Thr Gln Lys Ser Leu Ser Leu Ser Pro Gly Lys
225                 230                 235

<210> SEQ ID NO 6
<211> LENGTH: 39
<212> TYPE: PRT
<213> ORGANISM: Homo sapiens

<400> SEQUENCE: 6

Val Val Val Asp Val Ser His Glu Asp Pro Glu Val Lys Phe Asn Trp
1               5                   10                  15

Tyr Val Asp Gly Val Glu Val His Asn Ala Lys Thr Lys Pro Arg Glu
                20                  25                  30

Glu Gln Tyr Asn Ser Thr Tyr
            35

<210> SEQ ID NO 7
<211> LENGTH: 9
<212> TYPE: PRT
<213> ORGANISM: Homo sapiens

<400> SEQUENCE: 7

Arg Glu Gln Gln Tyr Asp Ser Thr Tyr
1               5

<210> SEQ ID NO 8
<211> LENGTH: 31
<212> TYPE: PRT
<213> ORGANISM: Artificial Sequence
<220> FEATURE:
<223> OTHER INFORMATION: Modified at all three Lys residues

<400> SEQUENCE: 8

Val Val Val Asp Val Ser His Glu Asp Pro His Glu Val Lys Phe Asn
1               5                   10                  15

Trp Tyr Val Asp Gly Val Glu Val His Asn Ala Lys Thr Lys Pro
                20                  25                  30

<210> SEQ ID NO 9
<211> LENGTH: 9
```

-continued

```
<212> TYPE: PRT
<213> ORGANISM: Artificial Sequence
<220> FEATURE:
<223> OTHER INFORMATION: Morfied at positions 2 and 6

<400> SEQUENCE: 9

Arg Glu Gln Gln Tyr Asn Ser Thr Tyr
1               5
```

HDC-SIGN BINDING PEPTIDES

CROSS REFERENCE TO RELATED APPLICATION

This application is a National Stage application under 35 U.S.C. §371 of International Application No. PCT/US/, having an International Filing Date of December, 2012, which claims priority of U.S. Provisional Application No. 61/577,495, filed on Dec. 19, 2011. The content of the application is incorporated herein by reference in its entirety.

GOVERNMENT INTERESTS

The invention disclosed herein was made, at least in part, with Government support under Grant No. NIH AI035875 from the National Institutes of Health. Accordingly, the U.S. Government has certain rights in this invention.

FIELD OF INVENTION

This invention relates to agents and methods for modulating immune responses by the immune system.

BACKGROUND OF INVENTION

The immune system defends the human body against pathogen infection, cellular transformation, and physical/chemical damage. Its dysfunction, either overactive or underactive, leads to various disorders. The dysfunction can be caused by aging, development defects, diseases, and medical treatment (e.g., chemotherapy or immuno-suppression). There is a need for drugs and reagents for treatment of immune disorders. The present invention addresses and meets the need by identifying DC-SIGN binding peptides that can modulate immune responses.

DC-SIGN (Dendritic Cell-Specific Intercellular adhesion molecule-3-Grabbing Non-integrin) is a C-type lectin receptor present on various immune cells, including macrophages and dendritic cells. DC-SIGN recognizes high-mannose glycans from a variety of pathogens, and acts as a pattern recognition receptor bridging innate and adaptive immunity (Geijtenbeek et al. *Nat Rev Immunol* 9, 465-479 (2009)). Ligation of DC-SIGN by bacteria-derived mannosylated glycans can induce their internalization, and also synergize with other innate receptor pathways promoting inflammation and resistance to infection. The immuno-suppressive potential of DC-SIGN has been documented following ligation by HIV8-derived gp120 or α-DC-SIGN antibody, which promotes the development of tolerogenic, IL-10 producing, dendritic cells, and interferes with TLR signaling (Gringhuis et al. *Immunity* 26, 605-24 616 (2007) and Hodges et al. *Nat Immunol* 27 8, 569-577 (2007)). Also, binding of IgG Fcs with glycans terminating in α2,6 sialic acids (sFc) to DC-SIGN results in an anti-inflammatory response (Kaneko et al. *Science* 313, 670-673 (2006) and Anthony et al. *Proc Natl Acad Sci USA* 13 105, 19571-19578 (2008)).

SUMMARY OF INVENTION

This invention relates to agents and methods for treating immune disorders, including immunodeficiency disorders or inflammatory disorders, e.g., autoimmune diseases.

Accordingly, one aspect of this invention features an isolated protein containing a first polypeptide chain that has the sequence of VVVDVSHEDPHEVKFNWYVDGVEVHNAKTKPREQQYNSTY (SEQ ID NO: 1). The first polypeptide chain can be about 40 to about 230 (e.g., 40-220, 40-200, 40-180, 40-150, 40-100, 40-80, 40-70, 40-60, 40-50, and 40-45, inclusive) amino acid residues (aa.) in length. The just mentioned sequence corresponds to aa. 261-300 of human IgG1 Fc. The first polypeptide chain can include additional fragment sequences from the human IgG1 Fc, but optionally is not the full-length human IgG1 Fc. In one example, the first polypeptide chain has the sequence of CVVVDVSHEDPHEVKFNWYVDGVEVHNAKTKPREQQYNSTY (SEQ ID NO: 2). In another example, the first polypeptide chain has the following sequence (SEQ ID NO: 3):

H-Cys-Val-Val-Val-Asp-Val-Ser-His-Glu-Asp-Phe-His-Glu-Val-Lys-Phe-Asn-Trp-Tyr-Val-Asp-Gly-Val-Glu-Val-His-Asn-Ala-Lys-Thr-Lys-Pro-Arg-Glu-Gln-Gln-Tyr-Asn-Ser-Thr-Tyr-OMe wherein R is wherein B is H, OH, or fucose. Shown below is the corresponding IgG1 Fc sequence, where the sequence of SEQ ID NO: 1 is underlined:

```
                                               (SEQ ID NO: 4)
EVQLVESDGGLVQPGRSLKLPCAASGFTFSDYYMAWVRQAPTKGLEWVAS

ISYDGSSTYYRDSVKGRFTISRDNAKSTLYLQMDSLRSEDTATYYCGRHS

SYFDYWGQGVMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPKPKDTL

MISRTPEVTCVVVDVSHEDPHEVKFNWYVDGVEVHNAKTKPREQQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK
```

In one embodiment, the above-described isolated protein further comprises a second polypeptide chain having the sequence of SEQ ID NO: 1, 2, or 3. The first polypeptide chain and the second polypeptide chain can have the identical sequence. The first polypeptide chain and the second polypeptide chain can form a dimmer via a disulfide bond or via other covalent or non-covalent means. In one example, the protein has the following structure:

In a third aspect, the invention features a method for enhancing immune response in a subject in need thereof. The method includes administering to the subject the protein mentioned above. This method can be used for treating immunocompromised individuals. The first polypeptide or the protein can be without an N-linked, complex biantennary glycan terminating with an α2,6 linked sialic acid. In one embodiment, the immune response is one directed to an antigen of interest and the method further comprises administering to the subject a composition containing the antigen.

In a fourth aspect, the invention features an immunogenic composition containing an antigen agent and an adjuvant agent, where the adjuvant agent contains the protein described above. The antigen agent can contain a polypeptide or a nucleic acid having a sequence encoding the polypeptide. Examples of the polypeptide include, but are not limited to, a pathogen protein (e.g., a bacterial protein or a viral protein) or a tumor antigen protein.

In a fifth aspect, the invention features a method of generating an immune response in a subject. The method includes administrating to a subject in need thereof the just-described immunogenic composition. As just mentioned, the immune response can be one directed to an antigen of interest, such as a viral protein or a tumor antigen protein. In that case, this method can be used for treating a cellular proliferative disorder in a subject. A cellular proliferative disorder refers to a disorder characterized by uncontrolled, autonomous cell growth, including malignant and non-malignant growth.

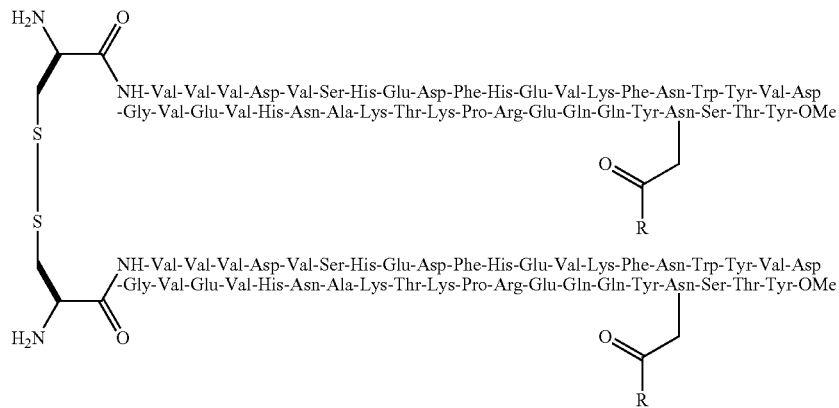

which is also shown in FIG. 2 below. In an embodiment, the first polypeptide chain consists essentially of or consists of the sequence of SEQ ID NO: 1, 2, or 3. The first polypeptide or the protein can be either with or without an N-linked, complex biantennary glycan terminating with an α2,6 linked sialic acid. The invention also features a composition containing the above-described isolated protein.

In a second aspect, the invention features a method for treating an inflammatory disorder, e.g., an autoimmune disease, in a subject in need thereof. The method includes, among others, a step of administering to the subject the protein or composition described above. The first polypeptide or the protein can have an N-linked, complex biantennary glycan terminating with an α2,6 linked sialic acid.

The invention features the isolated protein substantially as shown and described herein and methods of using the protein substantially as shown and described herein. Also provided are uses of the above-described proteins or compositions in the manufacture of a medicament for treating an inflammatory disorder in a subject in need thereof, for enhancing immune response in a subject in need thereof, or for treating a cellular proliferative disorder in a subject in need thereof.

The details of one or more embodiments of the invention are set forth in the description below. Other features, objects, and advantages of the invention will be apparent from the description and from the claims.

DESCRIPTION OF DRAWINGS

FIGS. 3A-D are a set of diagrams showing results from surface plasmon resonance (SPR) analysis.

DETAILED DESCRIPTION OF THE INVENTION

Figure 1:
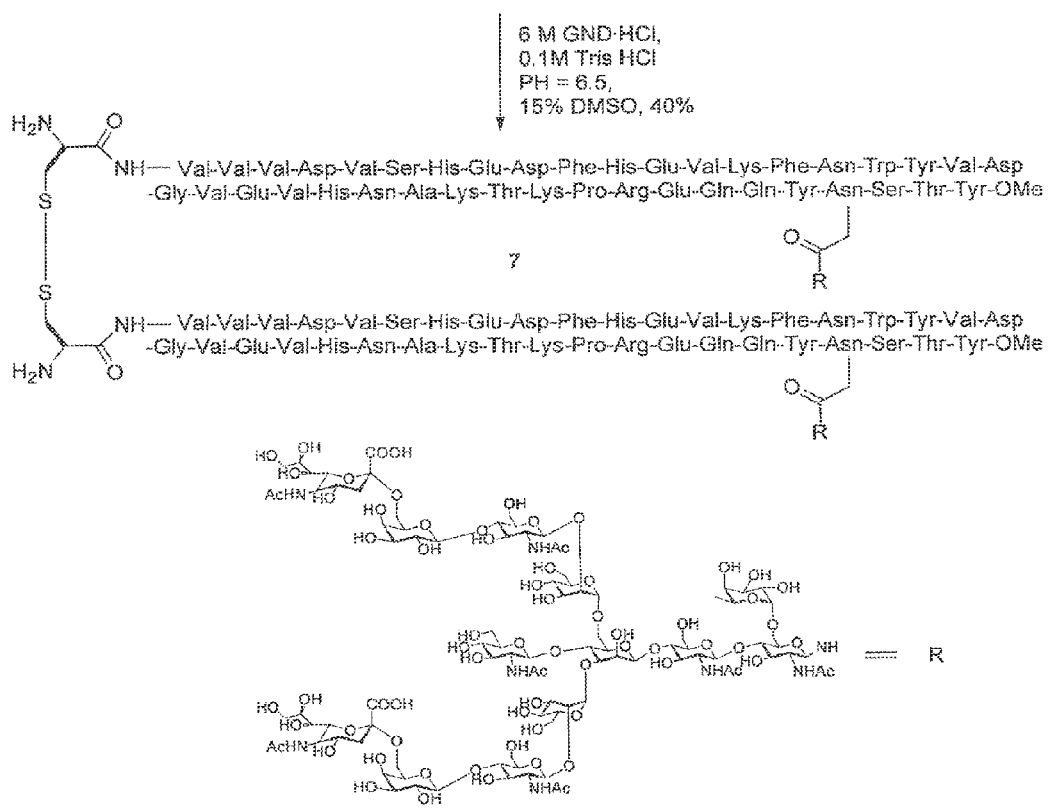
FIG. 1 is a diagram showing synthesis of a dimmer of a DC-SIGN-binding peptide derived from a human IgG1 fragment.

This invention relates to peptides, polypeptides, or proteins that bind to DC-SIGN and/or its homologues. DC-SIGN and its homologues have been identified as receptors that bind IgG antibodies or Fc fragments. They mediate intravenous immunoglobulin (IVIG)-related reversal of inflammation associated with various immune disorders. See U.S. Pat. No. 7,846,744, US Application Publication 2011007627, and Anthony et al. Nature, 2011 Jun. 19. doi: 10.1038/nature10134.

IVIG is a preparation containing pooled IgG purified from the plasma of blood donors. High dose IVIG (1-2 g/kg) is widely used for the suppression of autoantibody triggered inflammation in a variety of clinical settings (Nimmerjahn et al. *Annu Rev Immunol* 26, 513-533 (2008)). For example, it has been approved for the treatment of patients suffering from a number of autoimmune diseases, including immune-mediated thrombocytopenia, chronic inflammatory demyelinating polyneuropathy, and Guillain-Barre syndrome, as well as other autoimmune disorders. The anti-inflammatory activity of IVIG is triggered by a minor population of IgG Fcs, with glycans terminating in $\alpha 2,6$ sialic acids (sFc) that target myeloid regulatory cells expressing DC-SIGN (Kaneko et al. *Science* 313, 670-673 (2006); Anthony et al. *Science* 320, 373-376 (2008); and Anthony et al. *Proc Natl Acad Sci USA* 13 105, 19571-19578 (2008) and U.S. Pat. No. 7,846,744.)

DC-SIGN-Binding Peptides, Polypeptides, or Proteins

This invention is based, at least in part, on unexpected discoveries of novel DC-SIGN-binding peptides, polypeptides, or proteins, which can either recapitulate or interfere with the anti-inflammatory activity of IVIG/sFc. Those that recapitulate the anti-inflammatory activity of IVIG/sFc are agonists of DC-SIGN, while those that interfere with the anti-inflammatory activity are antagonists.

An "agonist" refers to a compound that interacts with a target to cause or promote an increase in the activation of the target. An agonist of DC-SIGN refers to an agent that binds to a DC-SIGN receptor and triggers a cellular response mediated by the receptor. Examples of a DC-SIGN receptor agonist include, but are not limited to, the 2.6 sialylated version of the above-mentioned peptide or protein, as well as its functional equivalents.

Conversely, an "antagonist" is a compound that binds to the receptor, but does not trigger the cellular response mediated by the receptor. Rather, an antagonist inhibits the function of an agonist in a competitive (e.g., by competing for a binding site or domain on DC-SIGN or its homologues) or non-competitive manner. Examples of a DC-SIGN receptor antagonist include, but are not limited to, the non-2.6 sialylated version of the above-mentioned peptide or protein, as well as its functional equivalents.

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation). The peptide, polypeptide, or protein "of this invention" include recombinantly or synthetically produced fusion versions having the particular domains or portions that bind to DC-SIGN. The term also encompasses polypeptides that have an added amino-terminal methionine (useful for expression in prokaryotic cells).

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

A functional equivalent of a peptide, polypeptide, or protein of this invention refers to a polypeptide derivative of the peptide, polypeptide, or protein, e.g., a protein having one or more point mutations, insertions, deletions, truncations, a fusion protein, or a combination thereof. It retains substantially the activity to of the above-mentioned agonist or antagonist DC-SIGN-binding peptides, polypeptides, or proteins, i.e., the ability to bind to the DC-SIGN receptor and to either trigger or interfere with the respective cellular response. The isolated polypeptide can contain SEQ ID NO: 1, 2, or 3 or a functional fragment thereof. In general, the functional equivalent is at least 75% (e.g., any number between 75% and 100%, inclusive, e.g., 70%, 80%, 85%, 90%, 95%, and 99%) identical to SEQ ID NO: 1, 2, or 3.

The amino acid composition of the above-mentioned agonist or antagonist peptide/polypeptide/protein may vary without disrupting the ability to bind to the respective receptor and trigger or inhibit the respective cellular response. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1, 2, or 3 is preferably replaced with another amino acid residue from the same side chain family. Alternatively, mutations can be introduced randomly along all or part of the sequences, such as by saturation mutagenesis, and the resultant mutants can be screened for the ability to bind to the respective receptor and trigger the respective cellular response to identify mutants that retain the activity as descried below in the examples.

Shown below is an exemplary human IgG1 Fc sequence, which has one or more conservative amino acid mutations:

```
                                              (SEQ ID NO: 5)
KVDKRVEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGK
```

The segment underlined (SEQ ID NO: 6) and the segment in bold (SEQ ID NO: 7) are variants of above mentioned SEQ ID NO: 1 and 2, respectively. As shown below, the sequence of SEQ ID NO: 6 has one deletion of (H) and one amino acid substitution (Q to E).

```
SEQ ID NO: 1:
VVVDVSHEDPHEVKFNWYVDGVEVHNAKTKPREQQYNSTY

SEQ ID NO: 6:
VVVDVSHEDP-EVKFNWYVDGVEVHNAKTKPREEQYNSTY
```

A polypeptide described in this invention can be obtained as a recombinant polypeptide. To prepare a recombinant polypeptide, a nucleic acid encoding it (e.g., SEQ ID NO: 1, 2, or 3) can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Figure 2:
FIG. 2 is a diagram showing synthesis of a dimmer of a DC-SIGN-binding peptide derived from a human IgG1 fragment with carbohydrate modifications.

Alternatively, the peptides/polypeptides/proteins of the invention can be chemically synthesized (see e.g., Creighton, "Proteins: Structures and Molecular Principles," W. H. Freeman & Co., NY, 1983), or produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984). In one example, the peptides/polypeptides/proteins can be chemically synthesized as shown in FIGS. 1 and 2.

The peptide/polypeptide/protein of this invention covers chemically modified versions. Examples of chemically modified peptide/protein include those subjected to conformational change, addition or deletion of a sugar chain, and those to which a compound such as polyethylene glycol has been bound. Once purified and tested by standard methods or according to the methods described in the examples below, the peptide/polypeptide/protein can be included in a pharmaceutical composition.

All of naturally occurring DC-SIGN-binding peptides/polypeptides/proteins, genetic engineered versions, and chemically synthesized versions can be used to practice the invention disclosed therein. DC-SIGN-binding peptides, polypeptides, or proteins obtained by recombinant DNA technology may have the same amino acid sequence as disclosed herein (e.g., SEQ ID NO: 1, or 3) or an functionally equivalent thereof. The term "DC-SIGN-binding peptides/polypeptides/proteins" covers those that can bind to DC-SIGN and/or its homologue. Such a DC-SIGN receptor or homologue may be any mammalian C-type lectin receptor type known to bind intracellular adhesion molecule (ICAM)-3 (CD50), including but not limited to DC-SIGN (a human dendritic cell-specific adhesion receptor (CD209) found on dendritic cells), SIGN-R1 (the murine homologue of DC-SIGN, known to be expressed on splenic marginal zone macrophages), and DC-SIGNR ("DC-SIGN-related," a human homologue of DC-SIGN expressed on sinusoidal endothelial liver cells and endothelial cells in lymph node tissue), as well as any relevant mammalian homologues or isoform thereof, such as well as various homologues, splice variants and/or isoforms, such as disclosed in US 2005/0221291 A1 (Ahuha et al).

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

As used herein, the term "Fc fragment" or "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and more preferably at least about 90% homology therewith, more preferably at least about 95% homology therewith, even more preferably, at least about 99% homology therewith.

The terms "Fc receptor" or "FcR" are used to describe a receptor that binds to the Fc region of an antibody. In one embodiment of the invention, FcR is a native sequence human FcR. In another embodiment, FcR, including human FcR, binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daron, Annu Rev Immunol, 15, 203-234 (1997); FcRs are reviewed in Ravetch and Kinet, Annu Rev Immunol, 9, 457-92 (1991); Capel et al., Immunomethods, 4, 25-34 (1994); and de Haas et al., J Lab Clin Med, 126, 330-41 (1995), Nimmerjahn and Ravetch 2006, Ravetch Fc Receptors in Fundamental Immunology, ed William Paul 5th Ed. each of which is incorporated herein by reference).

The term "lectin domain" or "LBD" may refer to a portion of a lectin domain, also referred to as the C-type lectin domain (see Geijtenbeek, et al., 2000, Cell 100:575-585) or carbohydrate-recognition domain (CRD; see Wu and KewalRamani, 2006, Nat. Rev. Immun. 6(11): 859-868) (e.g., from about amino acid 241-404 of human DC-SIGN) of a DC-SIGN receptor type. An LBD useful herein will be an LBD which may be have affinity for a known modulator.

Compositions

Within the scope of this invention is a composition that contains a suitable carrier and one or more of the agents described above. The composition can be a pharmaceutical composition that contains a pharmaceutically acceptable carrier or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

The above-described composition, in any of the forms described above, can be used for treating various immune disorders, including those characterized by inflammation. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas. The topical composition is useful for treating immune disorder in the skin, such as skin inflammatory disorders, including, but not limited to eczema, acne, rosacea, psoriasis, contact dermatitis, and reactions to poison ivy.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition. The topical composition may be a cosmetic or dermatologic product in the form known in the art for topical or transdermal applications, including solutions, aerosols, creams, gels, patches, ointment, lotion, or foam.

Uses

The above-described DC-SIGN-binding peptides, polypeptides, or proteins can be used in various ways. In particular, the can be used in modulating immune responses. For example, agonist DC-SIGN-binding peptides, polypeptides, or proteins can be used to suppress immune response while antagonist DC-SIGN-binding peptides, polypeptides, or proteins can be used to boost immune response.

Agonists

Agonist DC-SIGN-binding peptides, polypeptides, or proteins can be used for treating a subject having an inflammatory disorder. Inflammatory disorders, including autoimmune diseases, are disorders involving abnormal activation and subsequent migration of white blood cells to affected areas of the body. These conditions encompass a wide range of ailments that affect the lives of millions of people throughout the world. Although various treatments are presently available, many possess significantly side effects or are not very effective in alleviating all symptoms.

The term "inflammatory disorder" refers to a disorder that is characterized by abnormal or unwanted inflammation, such as an autoimmune disease. Autoimmune diseases are disorders characterized by the chronic activation of immune cells under non-activating conditions. Examples include psoriasis, inflammatory bowel diseases (e.g., Crohn's disease and ulcerative colitis), rheumatoid arthritis, psoriatic arthritis, multiple sclerosis, lupus, type I diabetes, primary biliary cirrhosis, and transplant.

Other examples of inflammatory disorders that can be treated by the methods of this invention include asthma, myocardial infarction, stroke, inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), acute respiratory distress syndrome, fulminant hepatitis, hypersensitivity lung diseases (e.g., hypersensitivity pneumonitis, eosinophilic pneumonia, delayed-type hypersensitivity, interstitial lung disease (ILD), idiopathic pulmonary fibrosis, and ILD associated with rheumatoid arthritis), and allergic rhinitis. Additional examples also include myasthenia gravis, juvenile onset diabetes, glomerulonephritis, autoimmune throiditis, ankylosing spondylitis, systemic sclerosis, acute and chronic inflammatory diseases (e.g., systemic anaphylaxis or hypersensitivity responses, drug allergies, insect sting allergies, allograft rejection, and graft-versus-host disease), and Sjogren's syndrome.

In particular, the invention relates to methods of treating one or more of the following immune disorders immune thrombocytopenia (ITP), autoimmune hemolytic anemia (AHA), systemic lupus erythematosus (SLE), Kawsaki's disease (an acute vasculitic syndrome), sclerodema, rheumatoid arthritis (RA), chronic inflammatory demylinating polyneuropathy (CIDP), pemphigus and other conditions associated with autoantibody mediated inflammation.

A subject to be treated for an inflammatory disorder can be identified by standard diagnosing techniques for the disorder. For example, the subject can be examined for the level or percentage of one or more of cytokines or immune cells in a test sample obtained from the subject by methods known in the art. To confirm the inhibition or treatment, one can evaluate and/or verify the level or percentage of one or more of the above-mentioned cytokines or cells in the subject after treatment.

Antagonists

Antagonist DC-SIGN-binding peptides, polypeptides, or proteins block the anti-inflammatory activity of sialylated Fc. Consequently, these antagonists can be used for treating immunocompromised individuals to enhance immune responses. For example, they can be used in improving the immune system for treating pathogen infection and cellular transformation. A cellular proliferative disorder refers to a disorder characterized by uncontrolled, autonomous cell growth, including malignant and non-malignant growth. Examples of this disorder include colon cancer, breast cancer, prostate cancer, hepatocellular carcinoma, melanoma, lung cancer, glioblastoma, brain tumor, hematopoietic malignancies, retinoblastoma, renal cell carcinoma, head and neck cancer, cervical cancer, pancreatic cancer, esophageal cancer, and squamous cell carcinoma.

More specifically, as the antagonists suppress DC-SIGN-mediated anti-inflammatory activity, they can be used to improve the body's immune system. An antagonist can be used alone or in combination with other compound, such as cytokines (e.g., TNF-$\alpha$., IL-8, IL-12, IL-2 and IL-6), to enhance the body's immune response. In particular, it can be used as an adjuvant agent or adjuvant. As used herein, the term "adjuvant agent" or "adjuvant" means a substance added to an immunogenic composition or a vaccine to increase the immunogenic composition or the vaccine's immunogenicity.

The adjuvant of the invention can be used to enhance the immune response to an antigen of a vaccine formulation. The adjuvant can be used with antigens derived from any bacteria or from any virus, provided that the antigen is not destroyed. The adjuvant is also useful in vaccine compositions that contain an antigen as described in U.S. Pat. Nos. 5,616,328 and 5,084,269. It may be useful in conjunction with any material that raises either humoral and/or cell mediated immune response, such as, for example, live viral, bacterial, or parasitic antigens; inactivated viral, tumor-derived, protozoal, organism-derived, fungal, or bacterial antigens, toxoids, toxins; self-antigens; polysaccharides; proteins; glycoproteins; peptides; cellular vaccines; DNA vaccines; recombinant proteins; glycoproteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease. Especially, materials such as recombinant proteins, glycoproteins, and peptides that otherwise do not raise a strong immune response can be used in connection with the adjuvant of the invention so as to elicit satisfactory response.

In certain embodiments, the above-mentioned antigen may be a cancer antigen or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-0017-1A/GA733, Carcinoembryonic Antigen (CEA) and its antigenic epitopes CAP-1 and CAP-2, etv6, am11, Prostate Specific Antigen (PSA) and its antigenic epitopes PSA-1, PSA-2, and PSA-3, prostate-specific membrane antigen (PSMA), T-cell receptor/CD3-.zeta. chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, am11, cyclophilin b), B cell lymphoma (Ig-idiotype), glioma (E-cadherin, α-catenin, β-catenin, gamma-catenin, and p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-0017-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

The adjuvant of the invention may be used in a vaccine formulation to immunize an animal. Thus, within the scope of this invention is an immunogenic or vaccine composition containing an antigenic agent and an adjuvant agent. The adjuvant agent contains one or more of the above-mentioned antagonists and, once administered to a subject, enhances the subject's immune response to the antigenic agent. The term "immunogenic" refers to a capability of producing an immune response in a host animal against an antigen or antigens. This immune response forms the basis of the protective immunity elicited by a vaccine against a specific infectious organism. "Immune response" refers to a response elicited in an animal, which may refer to cellular immunity (CMI); humoral immunity or both.

"Antigenic agent," "antigen," or "immunogen" means a substance that induces a specific immune response in a host animal. The antigen may contain a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin. The term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cattle), porcine (e.g., pigs), as well as in avians. The term "avian" refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary.

In one embodiment, the vaccine formulation contains the adjuvant of the invention and an antigen. The optimal ratios of each component in the vaccine formulation may be determined by techniques well known to those skilled in the art.

A vaccine formulation may be administered to a subject per se or in the form of a pharmaceutical or therapeutic composition. Pharmaceutical compositions comprising the adjuvant of the invention and an antigen may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen. For purposes of this application, "physiologically acceptable carrier" encompasses carriers that are acceptable for human or animal use without relatively harmful side effects (relative to the condition being treated), as well as diluents, excipients or auxiliaries that are likewise acceptable. Systemic formulations include those designed for administration by injection, e.g. subcutaneous, intradermal, intramuscular or intraperitoneal injection.

For injection, vaccine preparations may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing and/or dispersing agents. Alternatively, the antagonist DC-SIGN-binding peptides, polypeptides, or proteins may be in powder form for constitution with a suitable vehicle, e.g., sterile pyrogen-free water, before use.

Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the patient, but will typically range from about 0.1 mL to about 5 mL.

The above-described antagonists or compositions can be used as a medicament for treatment of immune system impairment. It may also be particularly helpful in individuals having compromised immune function. For example, the antagonists or compositions may be used for treating the opportunistic infections and tumors that occur after suppression of cell mediated immunity in, for example, transplant patients, cancer patients and HW patients.

It also can be used as a dietary supplement, health food, or health drink for prevention of immune system impairment. Subjects to be treated can be identified as having, or being at risk for acquiring, a condition characterized by immune system impairment, e.g., low level of spleen- or bone marrow-derived cells.

For example, patients undergoing chemotherapies or immune-suppressing therapies have low level of immune cells and often suffer from disorders associated with immune system impairment. To restore the immune cell level after the therapies, the patients can be treated with the antagonist or composition of this invention. In an ex vivo approach, the composition is administered to tissues (e.g., blood and bone marrow) or cells (e.g., tumor infiltrating lymphocytes or lymphokine-activated killer cells) obtained from a subject. The tissues or cells are then introduced back into the subject. In an in vivo approach, a composition of the invention is administered orally or by intravenous infusion, or injected or implanted subcutaneously, intramuscularly, intrathecally, intraperitoneally, intrarectally, intravaginally, intranasally, intragastrically, intratracheally, or intrapulmonarily. This treatment can be performed alone or in conjunction with other drugs or therapy.

The composition of the invention can also be used to therapeutically treat a condition treatable by a cell-mediated immune response. Such a therapeutic composition can be provided in further combination with one or more pharmaceutically acceptable carriers. Each component may be administered in any suitable conventional dosage form such as, for example, tablets, lozenges, parenteral formulations, syrups, creams, ointments, aerosol formulations, transdermal patches, transmucosal patches and the like. The composition can be administered as the single therapeutic agent in a treatment regimen. Alternatively, it can be administered in combination with another therapeutic composition, or with other active agents such as antivirals, antibiotics, etc. Because of its effect on while blood cells, the composition of this invention can be useful for treating viral diseases and tumors. This immunomodulating activity suggests that the immunogenic or vaccine composition of the invention is useful in treating conditions such as, but not limited to:

(a) viral diseases such as diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picomavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection; and (d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers.

Thus, the invention also provides a method of treating a viral infection in an animal and a method of treating a neoplastic disease (or cellular proliferative disorder) in an animal comprising administering a therapeutically effective amount of the immunogenic composition of the invention to the animal. Administration refers to intake of the antagonist or composition in any suitable form (e.g., pharmaceutical compositions, food product, beverage, and tablet). An effective amount refers to an amount of the above-described antagonist or composition that is sufficient to provide a therapeutic or healthful benefit, e.g., enhancing the proliferation of bone marrow or spleen cells (e.g., while blood cells) or reducing the probability of relapse after a successful course of treatment. A therapeutically effective amount to treat or inhibit a viral infection is an amount that will cause a reduction in one or more of the manifestations of viral infection, such as viral lesions, viral load, rate of virus production, and mortality as compared to untreated control animals. A therapeutically effective amount of a combination to treat a neoplastic condition is an amount that will cause, for example, a reduction in tumor size, a reduction in the number of tumor foci, or slow the growth of a tumor, as compared to untreated animals.

In one particular embodiment, the composition of the invention may be used to inhibit tumor growth in vivo. Subjects having tumor cells expressing a particular antigen may be immunized with a therapeutic combination that contains an antagonist and, optionally, the antigen. In some embodiments, the therapy can include an initial immunization and a second booster immunization.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

As used herein, "treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder.

An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The agent can be administered in vivo or ex vivo, alone or co-administered in conjunction with other drugs or therapy, i.e., a cocktail therapy. As used herein, the term "co-administration" or "co-administered" refers to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound or agent is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages can be in the range of, e.g., 0.01-100 mg/kg. Variations in the needed dosage are to be expected in view of the variety of compounds/agents available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

Example

A 40-amino acid peptide, corresponding to aa 261-300 of human IgG1 Fc, was synthesized as a monomer or disulfide-linked dimmer, with or without an N-linked, complex biantennary glycan terminating with an α2,6 linked sialic acid. Shown in FIG. 1 is the process of synthesizing a monomer (step 5) and a dimmer (step 7) of the peptide. Shown in FIG. 2 is the process of synthesizing a monomer (step 5) and a dimmer (step 7) of the peptide that were modified with modified carbohydrate.

Briefly, thioacid was used to couple tridecasaccharide with HOBT (Wang et al *J. Am. Chem. Soc.* 2011. 133, 1597.) and followed by removal of Fmoc by piperidine as shown below. This afforded the glycopeptide Arg292-Tyr300 in 73% yield.

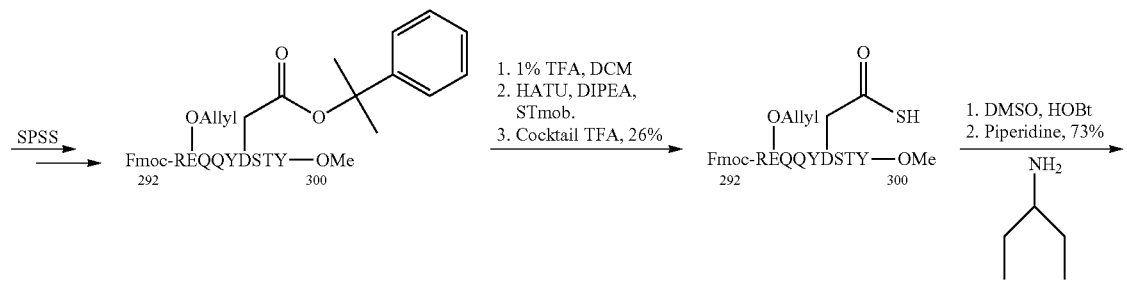

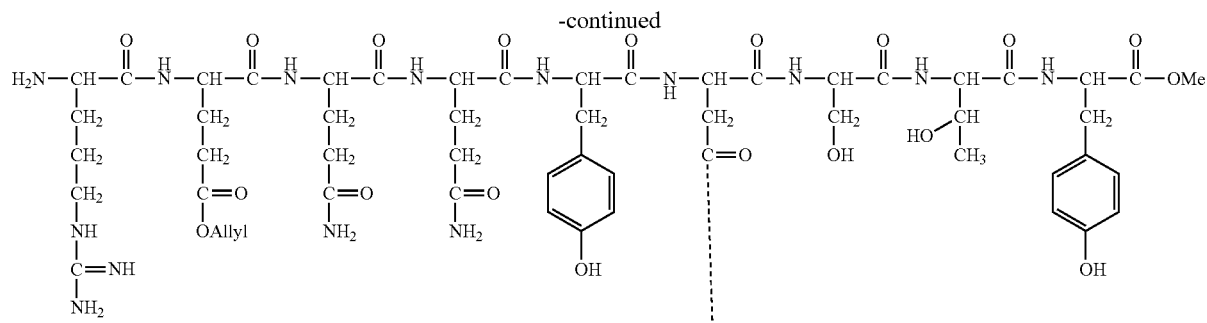

-continued

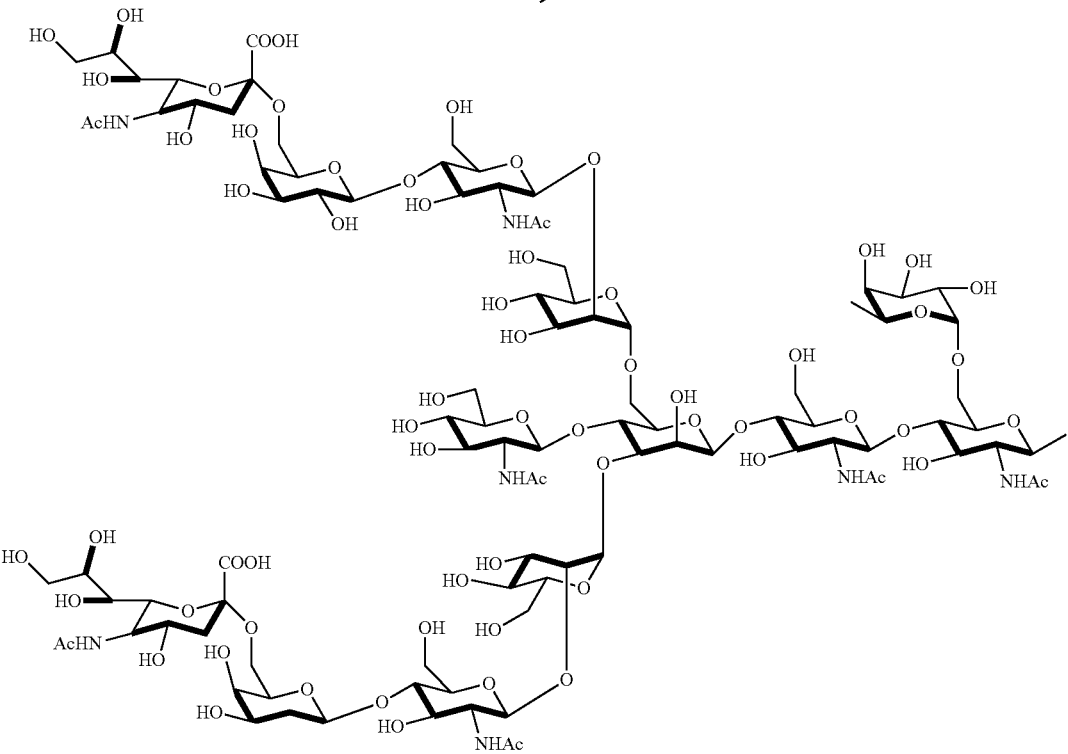

Then, as shown below, the glycopeptide (Arg292-Tyr300; SEQ ID NO: 7) was coupled to thioacid (Thz261-Pro291; SEQ ID NO: 8) with HOBT, which afforded the Thz261-Tyr300 glycopeptide in 57% yield (Wang et al *J. Am. Chem. Soc.* 2010, 132, 17045). Three alloc and one allyl protective group were removed by Pd(PPh₃)₄ and Thz was cleaved by MeONH$_2$ in 6 M GND/HCl buffer (PH=4.5), which afforded the fully deprotected sequence (Cys 261-Tyr300). Finally, the monomer was dimerized in 6 M GND buffer with 15% DMSO in PH 6.5.

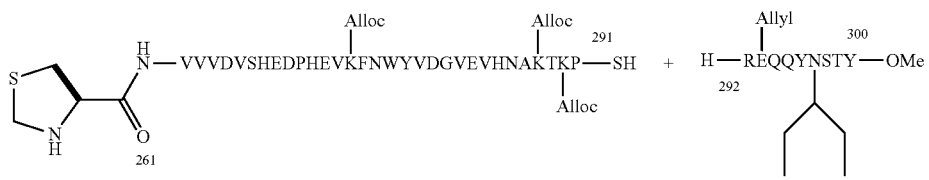

1. DMSO, HOBT, 57%.
2. Pd(PPh₃)₄, Ph₃SiH, DMSO, 42%.
3. MeONH₂ HCl, GND/HCl, TCEP 60%

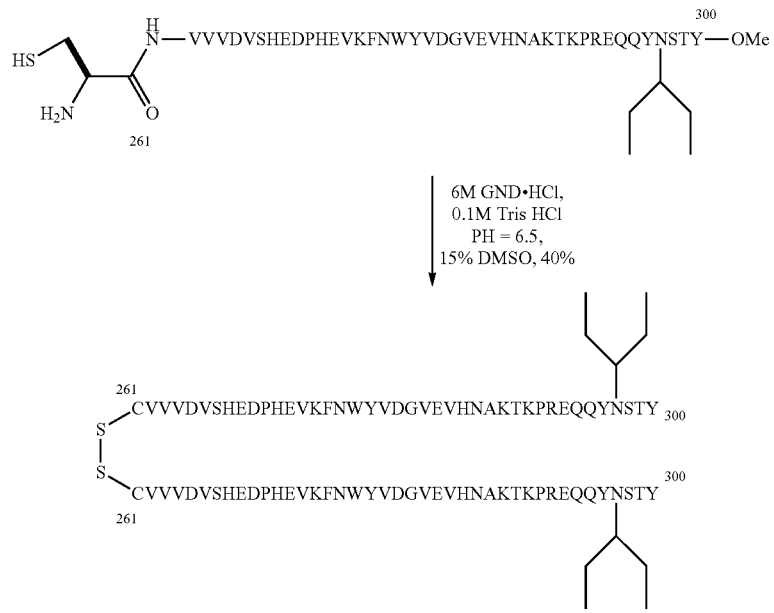

Figure 3A:
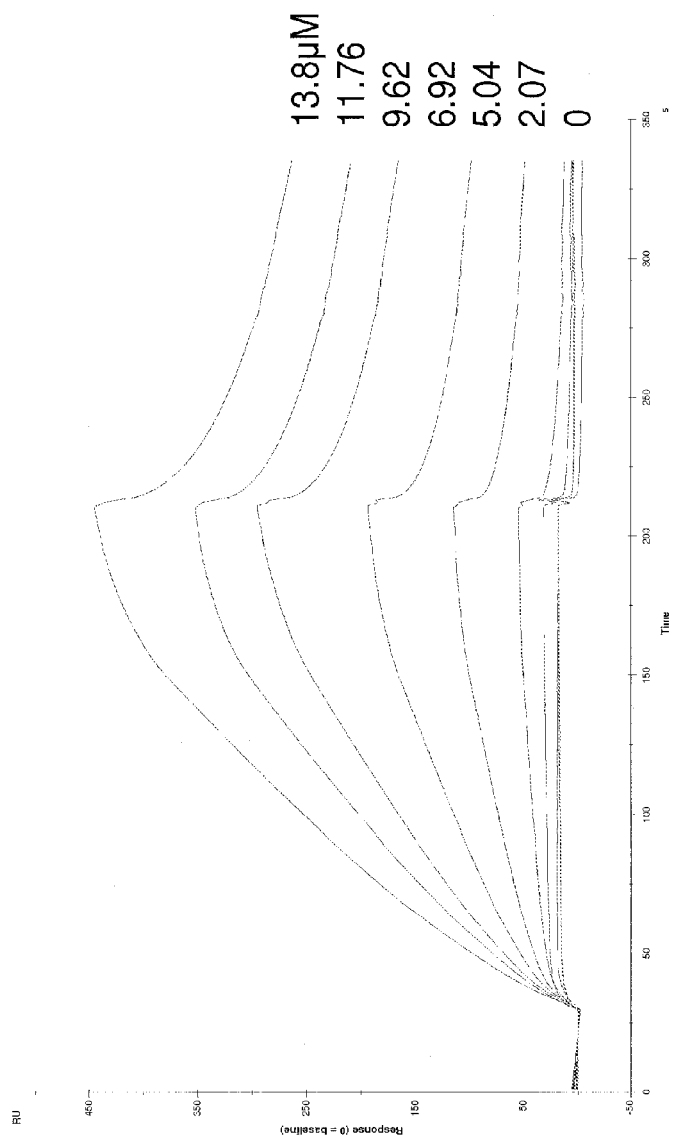
Figure 3B:
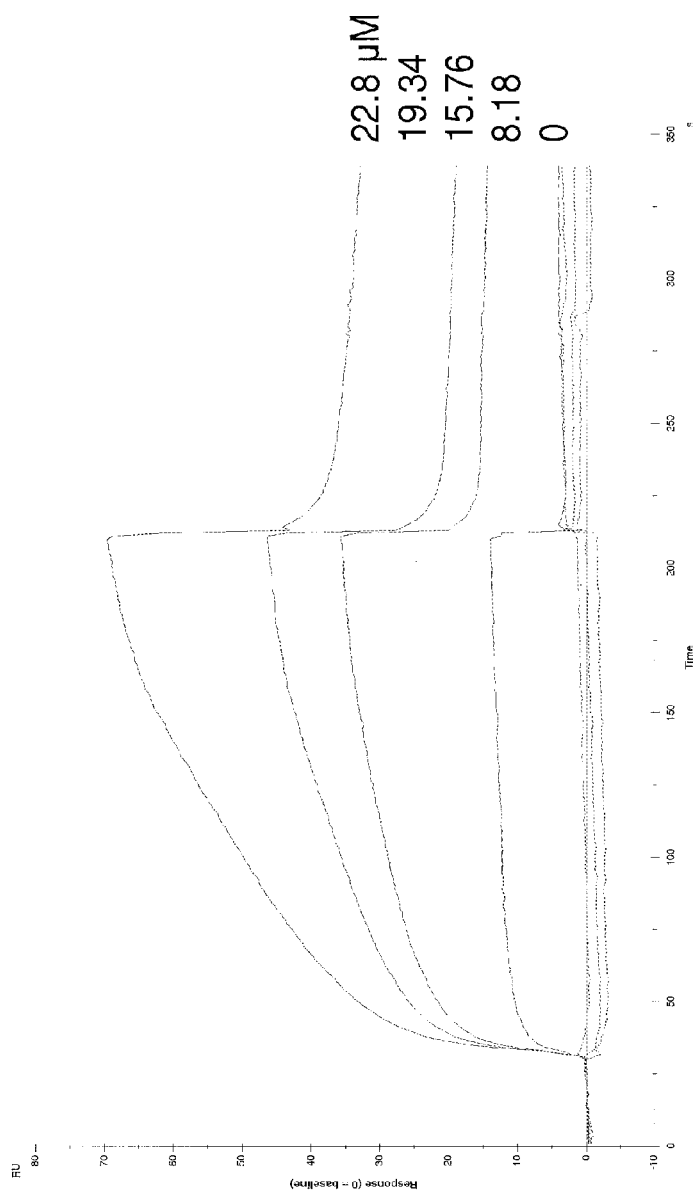
Figure 3C:
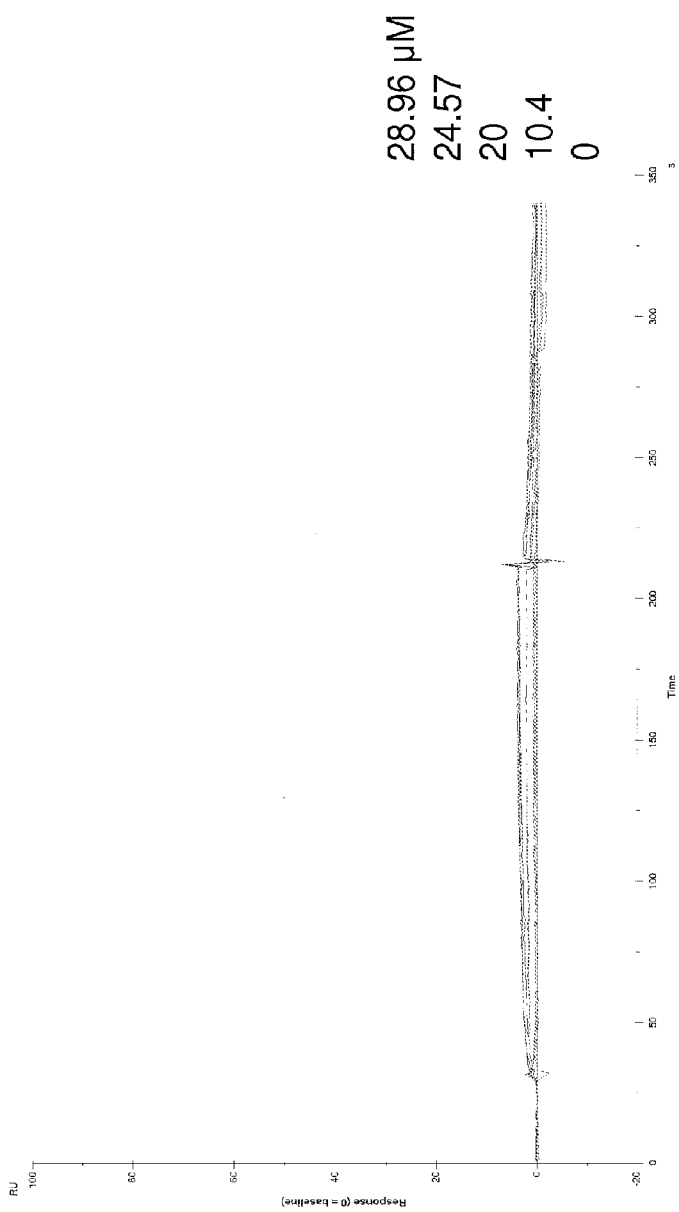

The monomer and dimmer were then examined for their activity to bind to human DC-SIGN using a surface plasmon resonance (SPR) analysis in the manner known in the art or in the manner disclosed in U.S. Pat. No. 7,846,744 and US Application Publication 20110076277. The contents of these two patent documents are incorporated by reference in their entirety. As shown in FIGS. 3A and B, both non-glycosylated Fc peptide dimmer (PW6-080) and non-glycosylated Fc peptide monomer (PW6-078) bound to DC-SIGN. In contrast, a peptide with a random sequence and sialylated glycan (PW3-256) did not bind to DC-SIGN, see FIG. 3C. It was also found that a synthetic α2,6 sialylated IgG peptide appeared to bind DC-SIGN with a reduced affinity as compared to a recombinant α2,6 sialylated Fc protein. See FIG. 3D.

DC-SIGN has previously been shown to bind to the intact Fc domain of human IgG1 when sialylated in an α2,6 linkage to the penultimate galactose of the complex, biantennary glycan attached at Asn 297 and mediate an anti-inflammatory response in mice challenged with an arthritogenic serum. The identification of this Fc-derived peptide capable of binding to DC-SIGN indicates that the sialylation of the Fc linked glycan results in the exposure of the peptide identified in this study to create a DC-SIGN binding ligand which is responsible for mediating the anti-inflammatory properties of sialylated Fc.

It was also found that a peptide of this invention competed with sialylated Fc for DC-SIGN and thereby blocked the anti-inflammatory activity of sialylated Fc. This result indicates that the peptide can be used for treating immunocompromised individuals by enhancing immune responses.

The foregoing example and description of the preferred embodiments should be taken as illustrating, rather than as limiting the present invention as defined by the claims. All publications cited herein are hereby incorporated by reference in their entirety. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. A number of embodiments of the invention have been described. Nevertheless, it will be understood that various modifications may be made without departing from the spirit and scope of the invention. Accordingly, other embodiments are within the scope of the following claims.

What is claimed is:

1. An isolated protein comprising a polypeptide chain comprising the sequence of SEQ ID NO: 1, wherein the polypeptide chain is about 40 to about 230 amino acid residues in length.

2. The isolated protein of claim 1, wherein the polypeptide chain comprises the sequence of SEQ ID NO: 2.

3. The isolated protein of claim 1, wherein the polypeptide chain comprises the following sequence (SEQ ID NO: 3):

H-Cys-Val-Val-Val-Asp-Val-Ser-His-Glu-Asp-Phe-His-Glu-Val-Lys-Phe-Asn-Trp-Tyr-Val-Asp
-Gly-Val-Glu-Val-His-Asn-Ala-Lys-Thr-Lys-Pro-Arg-Glu-Gln-Gln-Tyr-Asn-Ser-Thr-Tyr-OMe

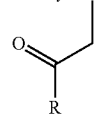

wherein R is

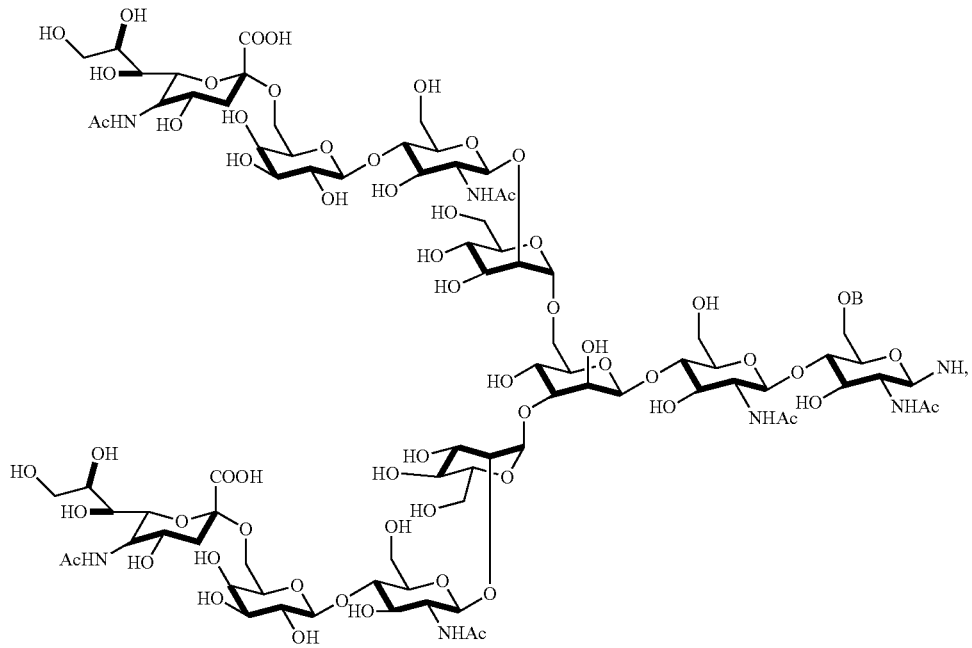

and wherein B is H, or fucose.

4. The isolated protein of claim 1 further comprising a second polypeptide chain comprising the sequence of SEQ ID NO: 1, 2, or 3.

5. The isolated protein of claim 4, wherein the polypeptide chains have the same sequence.

6. The isolated protein of claim 4, wherein the polypeptide chains form a dimer via a disulfide bond.

7. The isolated protein of claim 6, wherein the protein has the following structure:

wherein each R is:

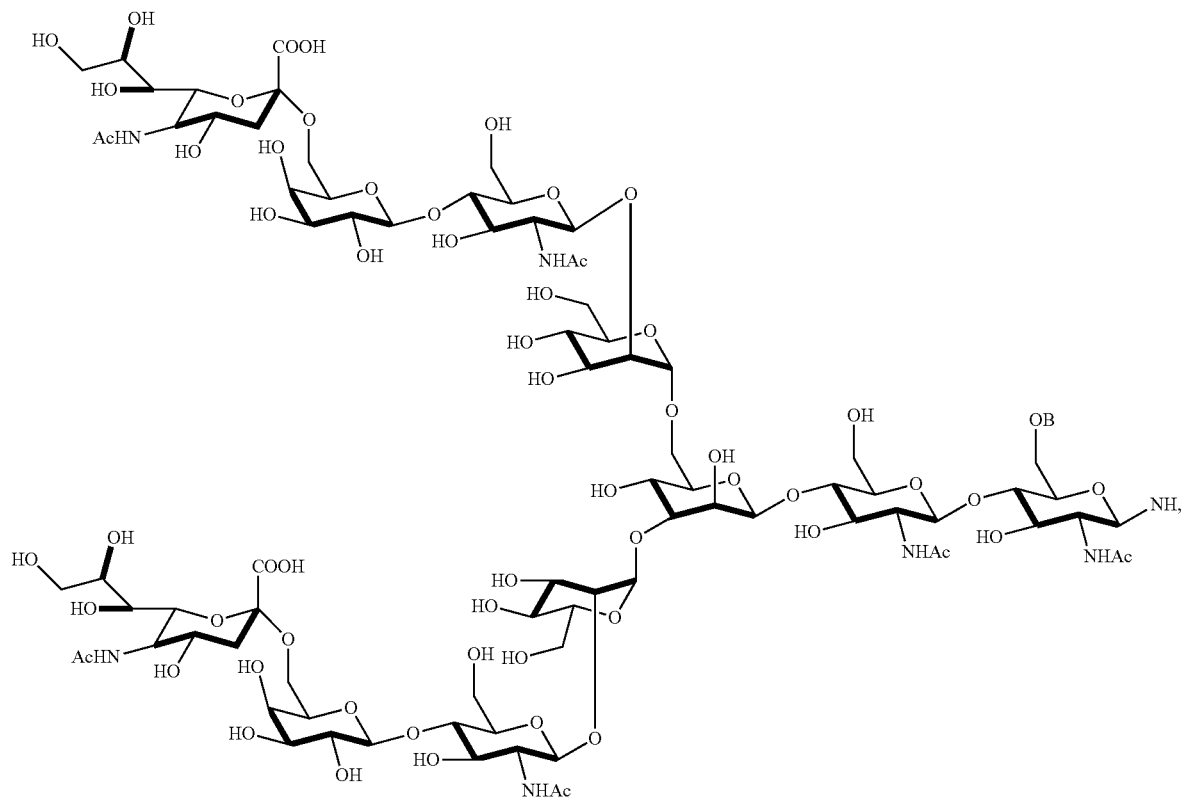

and each B is independently H or fucose.

8. The isolated protein of claim 1, wherein the polypeptide chain consists of the sequence of SEQ ID NO: 1, 2, or 3.

9. The isolated protein of claim 1, wherein the polypeptide chain is about 40 to about 100 amino acid residues in length.

10. The isolated protein of claim 9, wherein the polypeptide chain is about 40 to about 50 amino acid residues in length.

11. The isolated protein of claim 1, wherein the polypeptide lacks an N-linked, complex biantennary glycan terminating with an α2,6 linked sialic acid.

12. A composition comprising the isolated protein of claim 1.

13. A method for treating an inflammatory disorder in a subject in need thereof, comprising administering to the subject the protein of any of claims 1-10, wherein the protein has an N-linked, complex biantennary glycan terminating with an α2,6 linked sialic acid.

14. The method of claim 13, wherein the inflammatory disorder is an autoimmune disease.

15. A method for enhancing immune response in a subject in need thereof, comprising administering to the subject the protein of claim 1, wherein the protein lacks an N-linked, complex biantennary glycan terminating with an α2,6 linked sialic acid.

16. The method of claim 15, wherein the immune response is directed to an antigen and the method further comprises administering to the subject a composition comprising the antigen.

17. An immunogenic composition comprising an antigen agent and an adjuvant agent, wherein the adjuvant agent comprises the protein of claim 1.

18. The immunogenic composition of claim 17, wherein the antigen agent comprises an antigen polypeptide.

19. The immunogenic composition of claim 18, wherein the antigen polypeptide comprises a viral antigen or a tumor antigen.

20. A method of generating an immune response in a subject, comprising administrating to a subject in need thereof the immunogenic composition of claim 17.

21. A method for treating a cellular proliferative disorder in a subject, comprising administering to a subject in need thereof a therapeutically effective amount of the immunogenic composition of claim 17.

* * * * *